United States Patent [19]

Uijttewaal et al.

[11] 4,387,250

[45] Jun. 7, 1983

[54] PHOSPHONIUM SALTS, PROCESS FOR THEIR PREPARATION AND USE OF SAME AS STARTING MATERIALS FOR PREPARING UNSATURATED BICYCLIC COMPOUNDS

[75] Inventors: Arnoldus Uijttewaal, Geneva; Roger Snowden, Grand-Lancy, both of Switzerland

[73] Assignee: Firmenich SA, Geneva, Switzerland

[21] Appl. No.: 219,814

[22] Filed: Dec. 22, 1980

[30] Foreign Application Priority Data

Jan. 16, 1980 [CH] Switzerland ................. 332/80

[51] Int. Cl.³ ............................................. C07F 9/54
[52] U.S. Cl. ............................................. 568/2; 568/9
[58] Field of Search ................................... 568/2, 9

[56] References Cited

U.S. PATENT DOCUMENTS

| | | | |
|---|---|---|---|
| 2,945,069 | 7/1960 | Stern | 568/9 |
| 3,092,665 | 6/1963 | Wagner | 568/2 |
| 3,347,932 | 10/1967 | Chechak | 568/9 |
| 3,408,414 | 10/1968 | Surmatis | 568/9 X |
| 3,624,105 | 11/1971 | Surmatis et al. | 568/9 X |
| 4,049,669 | 9/1977 | Lam et al. | 568/9 X |
| 4,122,123 | 10/1978 | Hestermann et al. | 568/9 |

OTHER PUBLICATIONS

Zimmerman et al., J.A.C.S. 975497–5507 (1975).

*Primary Examiner*—Helen M. S. Sneed
*Attorney, Agent, or Firm*—Scully, Scott, Murphy & Presser

[57] ABSTRACT

New phosphonium salts useful as starting materials for preparing unsaturated bicyclic compounds. Process for their preparation.

1 Claim, No Drawings

PHOSPHONIUM SALTS, PROCESS FOR THEIR PREPARATION AND USE OF SAME AS STARTING MATERIALS FOR PREPARING UNSATURATED BICYCLIC COMPOUNDS

SUMMARY OF THE INVENTION

The invention relates to new phosphonium salts having the formula

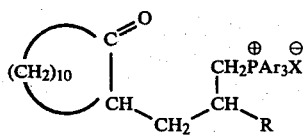

wherein symbol R represents a hydrogen atom or a methyl radical, Ar represents an aryl radical and X a halogen atom of a $BF_4$ or $ClO_4$ group.

The invention further relates to a process for preparing said compounds of formula (I) which comprises (A) reacting a compound of formula

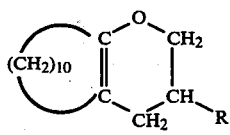

wherein symbol R is defined hereinabove with a phosphorus derivative having the formula

   (III)

wherein symbols X and Ar are defined hereinabove; or (B) reacting a compound of formula

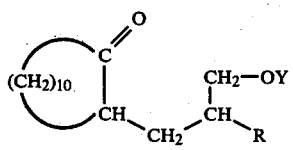

wherein symbol R is defined hereinabove and Y represents a tert-butyl, tetrahydropyranyl or trialkylsilyl radical with the phosphorus derivative of formula (III) defined sub letter (A); or (C) reacting a compound of formula

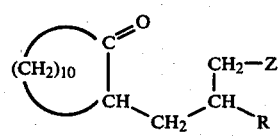

wherein symbol R is defined hereinabove and Z represents a halogen atom with a triaryl-phosphine.

The invention also relates to the use of said compounds of formula (I) as starting materials for the preparation of a compound of formula

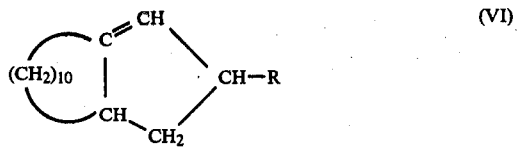

wherein symbol R represents a hydrogen atom or a methyl radical, which comprises reacting the said compound of formula (I) with a base.

The invention finally relates to new 14-methylbicyclo[10.3.0]pentadec-12-ene, viz. the compund of formula (VI) wherein R represents a methyl radical.

BACKGROUND OF THE INVENTION

EXALTONE® and muscone, two macrocyclic ketones, are very appreciated in the art for their elegant and tenacious musky odour. Both compounds have been known for several decades and since their discovery, a variety of syntheses have been proposed and described in the scientific literature [see e.g. J. Chem. Soc. 1964, 4154; Tetrahedron 20, 2601 (1964); Helv. Chim. Acta 50, 705 (1967) and Helv. Chim. Acta 50, 708 (1967)]. So far however, most of the published methods could not be sucessfully applied to their industrial scale preparation, especially in view of their complexity or in view of the low yields achieved in the critical reaction steps.

One of the prior known syntheses [Helv. Chim. Acta 50, 705 (1967)] is making use of the bicyclic hydrocarbon of formula

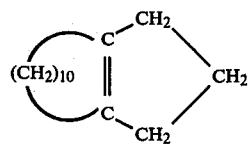

as intermediate in the synthesis of EXALTONE® (cyclopentadecanone), and of the corresponding methyl derivative of formula

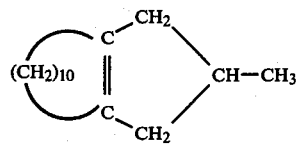

in the synthesis of muscone. Both intermediate compounds can be obtained from cyclododecanone, by a condensation reaction and a subsequent cyclization, hydrogenation and dehydrogenation. Due to rather poor overall yields however, such synthetic routes do not present any major interest to the industry.

The afore mentioned bicyclic hydrocarbons can in fact be prepared in a more rational and more advantageous manner, by reacting the above compounds of formula (VI) with an isomerizing agent such as a strong material or organic acid e.g.

PREFERRED EMBODIMENTS OF THE INVENTION

According to the process of the invention, method A, the starting compound of formula (II) is reacted with a phosphorus derivative of formula (III). Preferred phosphorus derivatives are those wherein symbol Ar is a phenyl radical, more particularly hydrogen-triphenyl-phosphonium bromide and hydrogen-triphenyl-phosphonium tetrafluoroborate. These phosphorus derivatives can be easily prepared from triphenyl-phosphine according to the usual techniques, for instance as described in Helv. Chim. Acta 45, 541 (1962) or Synthesis 1977, 628.

Compounds (II) and (III) can react in the presence of an inert organic solvent or not. Suitable solvents are aromatic hydrocarbons, toluene or xylene e.g. or mixtures of same, or dimethyl formamide or dioxanne e.g.

When the said reaction is effected in the presence of an inert organic solvent such as those defined hereinabove, the applied reaction temperature is equal or superior to about 110° C.: it generally corresponds to the boiling temperature of the solvent used.

The bicyclic compounds of formula (II) used as starting materials in the process of the invention are industrially available compounds. They can also be prepared according to known methods, for instance according to that disclosed in DE-OS No. 2,026,056.

According to another embodiment of the process of the invention, method B, the previously defined phosphorus derivative of formula (III) is reacted with a compound having the formula

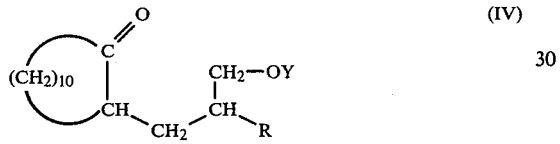

(IV)

wherein symbol Y represents a tert-butyl, a tetrahydropyranyl or trialkyl-silyl radical, in this latter case preferably a trimethyl-silyl radical. The said reaction is effected in the same conditions as those defined in variant A, preferably in the presence of an inert organic solvent such as an aromatic hydrocarbon, toluene or xylene e.g., at a temperature equal or superior to about 110° C.

According to a further embodiment of the process of the invention, method C, a triaryl-phosphine, preferably triphenyl-phosphine, is reacted with a compound of formula

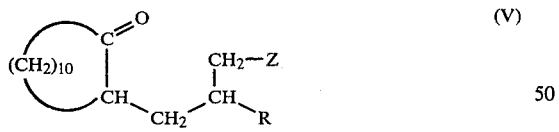

(V)

wherein symbol Z represents a halogen atom, preferably bromine, in the presence of an inert organic solvent such as an ether or a hydrocarbon or any other solvent suitable for a Wittig reaction. The compounds thus prepared are compounds of formula (I) wherein X represents a halogen atom and Ar represents a phenyl radical.

Compounds of formula (IV) and (V) used hereinabove as starting materials can be easily prepared from the corresponding hydroxy derivative (see in this respect DE-OS 2,026,056) according to conventional techniques or from cyclododecanone, by reacting same with the desired allylic derivative in the presence of free radicals initiators (see e.g. Synthesis 1976, 315 and references cited therein). The above mentioned preparative methods are illustrated by the following scheme wherein symbols R, Y and Z have the meaning previously given:

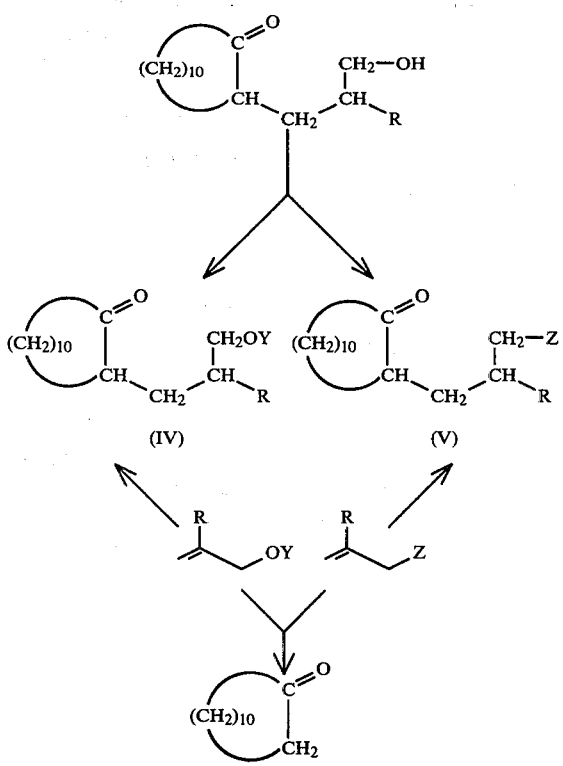

The preparation of said compounds of formula (IV) and (V) is also described in a detailed manner in the examples illustrating the invention.

As examples of compounds of formula (I) which can be prepared according to the process of the invention, one can cite

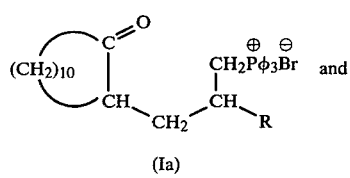

(Ia)

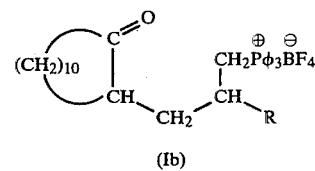

(Ib)

R = H or CH₃
φ = C₆H₅

The thus prepared phosphonium salts are stable cristalline or semi-cristalline compounds which can be isolated, identified and stored according to the conventional techniques.

According to the invention, the compounds of formula (I) are advantageously used as starting materials for preparing unsaturated bicyclic compounds of formula (VI). Said use consists in reacting the compounds of formula (I) with a base.

The said reaction can be effected according to the conditions usually applied for a Wittig reaction, i.e. by making use of an alcali metal hydride or alkoxide such as sodium hydride or methoxide, sodium or potassium tert-butoxide or tert-pentoxide e.g. An alkyl-lithium such as butyl-lithium e.g. also represents a suitable base as well as sodium amide in liquid ammonia or even potassium hydroxide.

The said reaction is effected in the presence of an inert organic solvent and, generally, under argon or nitrogen atmosphere. As inert organic solvents aromatic hydrocarbons or mixtures of aromatic hydrocarbons, ethers or amides can be conveniently used. Toluene or xylene are preferred.

The said reaction is effected moreover at a temperature equal or superior to about 80° C., more generally comprised between about 80° C. and the boiling temperature of the solvent or mixture of solvents used. The compounds of formula (VI) thus prepared can be isolated and purified according to the usual techniques, vapour phase chromatography or fractional distillation e.g.

The invention will be illustrated in a more detailed manner by the following examples wherein the temperatures are given in degrees centigrade.

EXAMPLE 1

Preparation of the compound of formula

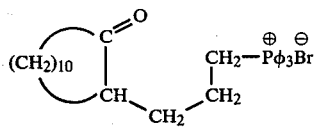

Method A 22.2 g (0.1 mole) of 13-oxa-bicyclo[10.4.0]hexadec-1(12)-ene and 34.5 g (0.1 mole) of hydrogen-triphenylphosphonium bromide—prepared according to the method given in Helv. Chim. Acta 45, 541(1962)—in 100 ml of xylene were heated to reflux for 24 hours. After cooling, filtration, washing of the precipitate with ether and final evaporation, there were obtained 56.1 g (ca 100% yield) of the desired compound (white crystals), m.p. 51°-58°.

IR: 1710, 1440, 1110 cm$^{-1}$.

NMR: 1.2 (14H, m); 1.6 (8H, m); 2.5 (3H, m); 3.8 (2H, m); 7.7 (15H, m) δ ppm

Method B 14.8 g (0.05 mole) of 2-(3-tert-butoxy-prop-1-yl)-cyclododecanone and 17.5 g (0.05 mole) of hydrogen-triphenylphosphonium bromide in 100 ml of xylene were heated at 120° for 70 hours. After cooling to room temperature, evaporation, treatment of the obtained residue with methylene chloride, then with petrol ether (30-50) and final evaporation under reduced pressure, there were isolated 23.5 g (83% yield) of the desired compound.

2-(3-Tert-butoxy-prop-1-yl)-cyclododecanone used hereinabove as starting material was prepared as follows: 2.8 g (0.025 mole) of 3-tert-butoxy-prop-1-ene and 1.5 g (0.025 mole) of di-tert-butyl-peroxide were added over a period of 1 hour to 18.2 g (0.1 mole) of cyclododecanone, at 140°. After heating for 1 further hour and final fractional distillation, the desired compound was isolated in a 80% yield.

B.p. 122°/13.3 Pascals $n^{20}_D$: 1.4749

NMR: 1.2 (9H, s); 1.3 (14H, m); 1.5 (8H, m); 2.5 (3H, m); 3.3 (2H, m) δ ppm

Method B 6.24 g (0.02 mole) of 2-(3-trimethyl-silyloxy-prop-1-yl)-cyclododecanone and 6.8 g (0.02 mole) of hydrogen-triphenyl-phosphonium bromide in 50 ml of xylene were heated to reflux for 50 hours. After cooling to room temperature, filtration and final evaporation under reduced pressure, there were isolated 10.8 g (96% yield) of the desired compound, m.p. 50° to 70°.

2-(3-Trimethyl-silyloxy-prop-1-yl)-cyclododecanone used hereinabove as starting material was prepared as follows: 32.5 g (0.25 mole) of 3-trimethyl-silyloxy-prop-1-ene in admixture with 14.6 g (0.25 mole) of di-tert-butyl-peroxide were added at 140° to 182 g (1 mole) of cyclododecanone (addition period: 6 hours). Fractional distillation of the reaction product finally gave the desired compound in a 75% yield.

B.p.: 110°-125°/6.65 Pascals $n^{20}_D$: 1.4713

IR: 2899, 1709, 1471, 1414, 1247 cm$^{-1}$

NMR: 0.15 (9H, s); 1.1-1.9 (21H, m); 2.2-2.8 (4H, m); 3.4-3.7 (2H, m) δ ppm

Method C 30.3 g (0.01 mole) of 3-(3-bromo-prop-1-yl)-cyclododecanone and 26.2 g (0.01 mole) of triphenylphosphine in 100 ml of toluene were heated to reflux for 24 hours. After the isolation and purification treatments previously described (Method A), there were obtained 83.3 g (96% yield) of the desired compound.

2-(3-Bromo-prop-1-yl)-cyclododecanone used hereinabove as starting material was prepared as follows: (a) 171.5 g (0.90 mole) of tosyl chloride were added under good stirring to a solution of 206.7 g (0.86 mole) of 2-(3-hydroxy-prop-1-yl)-cyclododecanone in 280 ml of pyridine cooled to 0°. After stirring at 0° to 10° for 3 further hours, the reaction mixture was kept overnight at 4°, then poured onto crushed ice and finally acidified with 600 ml of 36% aqueous HCl. After extraction with ether, drying of the organic layer over CaCl$_2$ and evaporation, there were isolated 273 g (81% yield) of 2-(3-p-toluene-sulfonyloxy-prop-1-yl)-cyclododecanone.

IR: 1710, 1605, 1355, 1185, 1175 cm$^{-1}$

NMR: 1.3 (14H, m); 1.5 (8H, m); 2.4 (3H, m); 2.4 (3H, s); 4.0 (2H, t, J=6 Hz); 7.3 (2H, d, J=9 Hz); 7.8 (2H, d, J=9 Hz) δ ppm (b) 297.3 g (0.75 mole) of the above compound and 90 g (1.0 mole) of butyl-bromide in 1 l of acetone were heated to reflux for 24 hours. After cooling, filtration and evaporation of the excess of solvent, 600 ml of water were added to the resulting mixture. After extraction with ether, washing with a saturated aqueous solution of sodium bisulfate, drying over Na$_2$SO$_4$ and final evaporation, there were isolated 213.1 g (93% yield) of the desired compound.

IR: 1710, 1480, 1445, 1245, 725 cm$^{-1}$

NMR: 1.3 (16H, m); 2.7 (6H, m); 2.5 (3H, m); 3.4 (2H, t, J=6 Hz) δ ppm

EXAMPLE 2

Preparation of the compound of formula

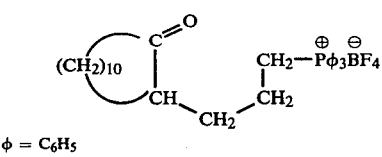

φ = C$_6$H$_5$ 22.2 g (0.1 mole) of 13-oxa-bicyclo[10.4.0]hexadec-1(12)-ene and 35 g (0.1 mole) of hydrogen-triphenyl-phosphonium tetrafluoroborate—prepared according to the method given in Synthesis 1977, 628—were heated at 170° for 24 hours. After cooling, washing of the residue with methylene chloride, then with ether, filtration of the precipitate and evaporation under reduced pressure, there were isolated 52.7 g (92% yield) of the desired compound (white crystals), m.p. 57°–85°.

IR: 1705, 1440, 1110, 1070 cm$^{-1}$

NMR: 1.2 (14H, m); 1.6 (8H, m); 2.5 (3H, m); 3.2 (2H, m); 7.7 (15H, m) δ ppm

EXAMPLE 3

Preparation of the compound of formula

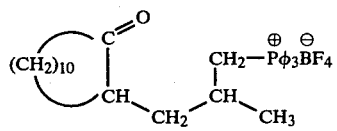

φ = C$_6$H$_5$ 13.9 g (0.059 mole) of 15-methyl-13-oxa-bicyclo[10.4.0]hexadec-1(12)-ene and 20.6 g (0.059 mole) of hydrogen-triphenyl-phosphonium tetrafluoroborate were heated at 170° for 24 h. After cooling and subsequent treatments as described in Example 2, there were isolated 34.5 g (100% yield) of the desired compound (white crystals), m.p. 63°–69°.

IR: 1710, 1440, 1080 cm$^{-1}$

NMR: 0.9 (3H, d, J=6 Hz); 1.2 (14H, m); 1.6 (7H, m); 2.3 (2H, m); 2.7 (1H, m); 3.2 (2H, dxd, J$_1$=13 Hz, J$_2$=6 Hz); 7.7 (15H, m) δ ppm The above identified phosphonium salt was also obtained as follows: 23.6 g (0.1 mole) of 15-methyl-13-oxa-bicyclo[10.4.0]hexadec-1(12)-ene and 35.0 g (0.1 mole) of hydrogen-triphenyl-phosphonium tetrafluoroborate in 100 ml of xylene were heated to reflux for 18 hours. After evaporation, there were isolated 45 g (77% yield) of the desired compound.

EXAMPLE 4

Preparation of the compound of formula

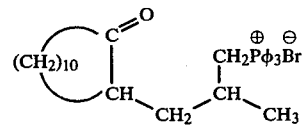

φ = C$_6$H$_5$ 9.8 g (0.03 mole) of 2-(2-methyl-3-trimethyl-silyloxy-prop-1-yl)-cyclododecanone and 10.3 g (0.03 mole) of hydrogen-triphenyl-phosphonium bromide were heated at 140°–150° for 15 hours. After cooling, acidification of the resulting mixture, treatment with methylene chloride and evaporation under reduced pressure, there were isolated 16 g (95% yield) of the desired compound (white crystals), m.p. 60°–90°.

IR: 1705, 1440, 1110 cm$^{-1}$

NMR: 0.9 (3H, d, J=6 Hz); 1.2 (14H, m); 1.6 (7H, m); 2.3 (2H, m); 2.7 (1H, m); 3.8 (2H, dxd, J$_1$=13 Hz, J$_2$=6 Hz); 7.7 (15H, m) δ ppm 2-(2-Methyl-3-trimethyl-silyloxy-prop-1-yl)-cyclododecanone used hereinabove as starting material was prepared from cyclododecanone and 2-methyl-3-trimethyl-silyloxy-prop-1-ene according to the process given in Example 1 (method B).

B.p. 120°–130°/6.65 Pascals n$^{20}$$_D$=1.4700

IR: 2899, 1709, 1466, 1361, 1247 cm$^{-1}$

NMR: 0.15 (9H, s); 0.9 (3H, d, J=6 Hz); 1.1–2.0 (20H, m); 2.2–2.9 (4H, m): 3.3 (2H, d) δ ppm

EXAMPLE 5

Preparation of bicyclo[10.3.0]pentadec-12-ene 6.6 g (0.15 mole) of sodium hydride (55% dispersion in mineral oil) were first added dropwise to 13.2 g (0.15 mole) of tert-amyl alcohol, then heated for 1 hour at 70°. The thus obtained mixture was then added dropwise and under nitrogen atmosphere to 11.35 g of the compound of Example 1 in 50 ml of toluene (addition period: 30 min.; addition temperature: 70°). The reaction mixture was heated to reflux for 3 further hours, then cooled to room temperature and finally hydrolyzed with 100 ml of water. After extraction with petrol ether (30–50), drying of the organic phase and distillation, there were isolated 2.7 g (66% yield) of the desired compound, b.p. 110°/6.65 Pascals.

n$^{23}$$_D$=1.5078

IR: 1650, 835 cm$^{-1}$

NMR: 1.3 (20H, m); 2.2 (4H, m); 2.7 (1H, m); 5.4 (1H, m) δ ppm

The above identified compound was found identical with a pure sample prepared according to J. Amer. Chem. Soc. 79, 5558, (1957).

Bicyclo[10.3.0]pentadec-12-ene thus prepared can be converted into bicyclo[10.3.0]pentadec-1(12)-ene as follows: 191 g of the above compound in 500 ml of toluene were heated to reflux for 6 hours, in the presence of 10 g of benzene-sulfonic acid. After cooling, washing with aqueous NaHCO$_3$, evaporation and distillation, there were isolated 168.2 g (88% yield) of the desired compound, b.p. 80°–90°/6.55 Pascals.

n$^{23}$$_D$: 1.5062

NMR: 1.3 (18H, m); 2.2 (8H, m) δ ppm

MS: M$^+$=206(67); m/e: 135(22), 121(31), 94(52), 82(75), 81(63), 80(100), 67(57), 55(33), 41(54)

The above identified compound was found identical with a pure sample prepared according to J. Amer. Chem. Soc. 79, 5558 (1957).

EXAMPLE 6

Preparation of bicyclo[10.3.0]pentadec-12-ene

The process of Example 5 was repeated under different conditions: the nature of the base, the nature of the solvent and the concentration, namely, have been modified. The obtained results are summarized in the following table: in said table, the proportions of base (g) and solvent (ml) are given for 100 g of starting material.

| Starting material | Base (g) | Solvent (ml) | Reaction conditions | Yield (%) |
|---|---|---|---|---|
| Compound according to Example 1[1] | potassium tert-butoxide (21) | xylene (177) | 4 h at 120° | 73 |
| Compound according to Example 1[1] | sodium methoxide (42) | xylene/DMF[2] (195)/(59) | 4 h at 130°[3] | 74 |
| Compound according to Example 2 | sodium tert-pentoxide (38) | toluene (350) | 3 h at 110° | 60 |
| Compound according to Example 2 | sodium methoxide (95) | xylene/DMF[2] (877)/(88) | 3 h at 140° | 68 |
| Compound according to Example 2[1] | sodium tert-pentoxide (38) | xylene (175) | 20 h at 140° | 58 |

[1] raw material
[2] dimethyl-formamide
[3] with simultaneous distillation of methyl alcohol

EXAMPLE 7
Preparation of 14-methyl-bicyclo[10.3.0]pentadec-12-ene 34.5 g of the compound of Example 3 in 100 ml of toluene were first heated to reflux under nitrogen atmosphere. 12.7 g (0.116 mole) of sodium tert-pentoxide were then progressively added to the above mixture which was finally heated to reflux for 4 further hours. After cooling to room temperature, addition of 75 ml of water, successive treatments with methylene chloride and petrol ether (30–50), filtration and final distillation, there were isolated 6.4 g (50% yield) of the desired compound.

$n^{23}_D$: 1.5042

IR: 1650, 835 cm$^{-1}$

NMR: 1.0 (15H, d, J=6 Hz); 1.1 (1.5H, d, J=6 Hz); 1.4 (18H, m); 2.1 (2H, m); 2.7 (2H, m); 5.3 (1H, m) δ ppm MS: M+=220(38); m/e: 205(10), 135(10), 107(45), 94(100), 93(53), 81(35), 67(20), 55(21), 41(27)

14-Methyl-bicyclo[10.3.0]pentadec-12-ene thus prepared can be converted into 14-methyl-bicyclo[10.3.0]pentadec-1(12)-ene as follows:

15.0 g (0.068 mole) of the above compound in 100 ml of toluene were heated to reflux for 6 hours, in the presence of 2.5 g of benzene sulfonic acid. After cooling, washing with aqueous NaHCO$_3$, evaporation and final distillation, there were isolated 12.8 g (85% yield) of the desired compound, b.p. 100°–110°/1.33 Pascals.

NMR: 1.0 (3H, d, J=6 Hz); 1.3 (17H, m); 2.2 (8H, m) δ ppm

MS: M+=220(100); m/e: 205(6), 163(8), 149(20), 135(29), 121(26), 107(66), 94(98), 93(79), 81(89), 67(52), 55(67), 41(77)

The above identified compound was found identical with a pure sample prepared according to Chem. Abstr. 70, 88108 v (1970).

What we claim is:

1. Compounds of formula wherein symbol R represents a hydrogen atom or a methyl radical, Ar represents an aryl radical and X a halogen atom or a BF$_4$ or ClO$_4$ group.

* * * * *